(12) United States Patent
Turner et al.

(10) Patent No.: US 6,248,736 B1
(45) Date of Patent: Jun. 19, 2001

(54) 4-OXO-1,4-DIHYDRO-3-QUINOLINECARBOXAMIDES AS ANTIVIRAL AGENTS

(75) Inventors: Steven Ronald Turner, Kalamazoo; Joseph Walter Strohbach, Mendon; Suvit Thaisrivongs, Kalamazoo; Valerie A. Vaillancourt, Kalamazoo; Mark E. Schnute, Kalamazoo; Allen Scott, Kalamazoo, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/465,670

(22) Filed: Dec. 17, 1999

Related U.S. Application Data

(60) Provisional application No. 60/140,614, filed on Jun. 23, 1999, provisional application No. 60/138,390, filed on Jun. 9, 1999, and provisional application No. 60/115,113, filed on Jan. 8, 1999.

(51) Int. Cl.[7] .................................................. A61K 31/54
(52) U.S. Cl. .................................... 514/226.8; 514/228.2; 514/231.5; 514/312; 514/314; 544/55; 544/62; 544/96; 544/111; 546/153
(58) Field of Search .............................. 514/226.8, 228.2, 514/231.5, 312, 314; 544/55, 62, 96, 111; 546/153

(56) References Cited

U.S. PATENT DOCUMENTS 5,175,151   12/1992   Afonso et al. .
5,328,887   7/1994    Janssens et al. .
5,891,878   4/1999    Beasley et al. .

FOREIGN PATENT DOCUMENTS

| WO97/14682 | 4/1997 | (WO) | ........................... C07D/215/56 |
| WO98/23608 | 6/1998 | (WO) | ........................... C07D/401/12 |
| WO99/32450 | 7/1999 | (WO) | ........................... C07D/215/56 |

*Primary Examiner*—Richard L. Raymond
*Assistant Examiner*—Tamthom N. Truong
(74) *Attorney, Agent, or Firm*—Lucy X. Yang

(57) ABSTRACT

The present invention provides a compound of formula I

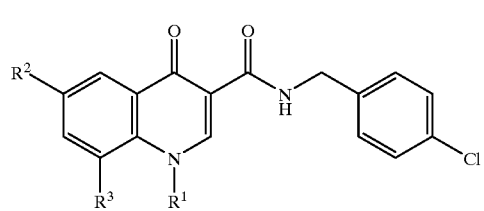

Wherein $R^1$ is $C_{1-7}$ alkyl, optionally substituted by hydroxy or $NR^4R^5$; $R^2$ is $C_{1-7}$ alkyl substituted by hydroxy or $NR^4R^5$; $R^3$ is H, F or $C_{1-7}$ alkoxy; $R^4$ and $R^5$ together with N are a 5- or 6-membered heterocyclic moiety having 1–3 heteroatoms selected from the group consisting of nitrogen, oxygen and sulfur in which sulfur may be substituted by one (1) or two (2) oxygen atoms; and pharmaceutically acceptable salts thereof Compounds of formula I of the present invention are useful as antiviral agents.

17 Claims, No Drawings

4-OXO-1,4-DIHYDRO-3-QUINOLINECARBOXAMIDES AS ANTIVIRAL AGENTS

CROSS-REFERENCE TO RELATED APPLICATIONS

This application claims the benefit of the following provisional application(s): U.S. Ser. No. 60/140,614, filed Jun. 23, 1999; U.S. Ser. No. 60/138,390, filed Jun. 9, 1999; and 60/115,113, filed 8 Jan. 1999, under 35 USC §119(e)(i).

FIELD OF THE INVENTION

The present invention provides 4-oxo-1,4-dihydro-3-quinolinecarboxamide derivatives, more specifically, provides (4-chlorobenzyl)-4-oxo-1,4-dihydro-3-quinolinecarboxamide of formula I. These compounds are useful as antiviral agents, in particular, as agents against viruses of the herpes family.

BACKGROUND OF THE INVENTION

The herpesviruses comprise a large family of double stranded DNA viruses. They are the source of the most common viral illnesses in man. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Kaposi's sarcoma, body cavity based lymphomas, and multiple myeloma.

Compounds of the present invention are distinct from all other hydroxyquinoline pharmaceutical agents in that the unique position of chloro substitutent on the N-phenylmethyl of formula I is critical for having useful antiviral activities. These compounds are useful to treat or prevent the above referenced herpesviral infections, particularly, human cytomegaloviral infection.

INFORMATION DISCLOSURE

U.S. Pat. No. 5,891,878 discloses the use of compounds of structure 1 for the treatment of a disease state capable of being modulated by inhibition of production of phosphodiesterase IV or tumor necrosis factor,

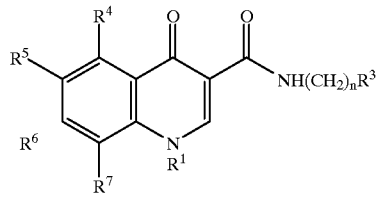

1 wherein $R^1$ may be alkyl(1–6), alkyl(1–6)cycloalkyl, alkyl(1–6)heterocycle, alkyl(1–6)aryl or alkyl(1–6)heteroaryl each optionally substituted by halogen, alkoxy, hydroxy, CN, $CO_2H$ or corresponding ester or amide, alkyl(1–6), $NR^9R^{10}$, $SO_2NR_2$; $R^3$ may be phenyl, pyridyl, furyl, pyrazinyl, pyridazinyl, pyrimidinyl, or cycloalkyl(3–10) which may be optionally substituted by halogen, alkoxy (1–6), OH, CN, $CO_2H$ and corresponding esters or amides, alkyl(1–6), haloalkyl(1–6), $NR^9R^{10}$, $SO_2NR_2$, aryl, heteroaryl, cycloalkyl heterocyclo, or may be fused to a second carbocyclic or heterocyclic ring; $R^{4-7}$ may be hydrogen, halogen, alkoxy(1–6), hydroxy, CN, $CO_2H$, $CO_2$alkyl(1–6), CONHalkyl(1–6), CONdialkyl(1–6), $NR^9R^{10}$, or alkyl(1–6) in which alkyl may be substituted by halogen, alkoxy(1–6), hydroxy, CN, $CO_2$alkyl(1–6), CONHalkyl(1–6), CONdialkyl(1–6), $NR_9R_{10}$, $SO_2NR_2$; any two adjacent substituent $R^{4-7}$ may form a 5–7 membered ring containing 0, 1, or 2 heteroatoms; $R^{9-10}$ may be hydrogen, alkyl(1–6), aryl, heteroaryl, $COCF_3$, $SO_2CF_3$, cycloalkyl, alkylcarbonyl, arylcarbonyl, alkoxycarbonyl, arylsulfonyl, alkylsulfonyl; or $NR^9R^{10}$ may form a 5 or 6 membered ring such as a pyrrolidine, piperidine, morpholine, or piperazine ring; n may be 0–3.

U.S. Pat. No. 5,175,151 discloses compounds of structure 2 as antiviral and antihypertensive agents,

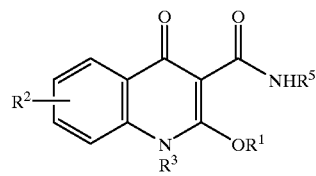

2 wherein $R^1$ may be alkyl, alkenylhalide, $(CH_2)_nCO_2R$, or $(CH_2)_nNR^6R^7$ where $R^6$ and $R^7$ may be hydrogen or alkyl; $R^2$ may include alkyl, alkoxy, aryloxy, aryl, aralkyl, halogen, acyloxy, amino optionally substituted, hydroxy, $CH_2OH$, $CO_2H$, alkylesters, $CF_3$; $R^3$ may be alkyl, aralkyl, optionally substituted aryl, alkylheteroaryl, $(CH_2)_nCO_2R$, or $(CH_2)_n$OH; $R^5$ may be hydrogen, alkyl, aryl, aralkyl, heteroaryl, heteroalkyl, or alkoxy. The patent actually claims a significantly narrower scope which does not include 3-carboxamides.

PCT publication WO 97/14682 describes compounds useful as gronadotropin-releasing hormone antagonists according to the generic structure 3

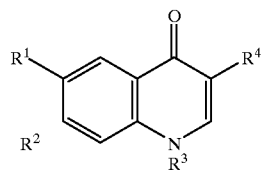

3 wherein, $R^1$ is a substituent according to the formula $XNR^5R^6$ where X is an alkylene or alkyl group optionally substituted by halogen, $R^5$ is an aralkyl substituent, and $R^6$ is an alkyl substituent; $R^2$ is an acylaminoaryl substituent; $R^3$ is a halogenaralkyl substituent; and $R^4$ is a carbonyl group optionally esterified or amidated for which $NHCH_2Ph$ is specified in the disclosure.

U.S. Pat. No. 5,328,887 discloses compounds for the use in a thermal transfer process which would include substructure 4 wherein R may be an optionally substituted hydrocarbon group; R' may be an optionally substituted carboxamide; and the quinoline ring may be optionally substituted.

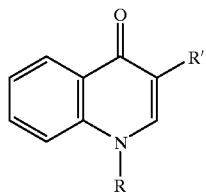

PCT publication, WO 98/23608 discloses compounds of structure 5

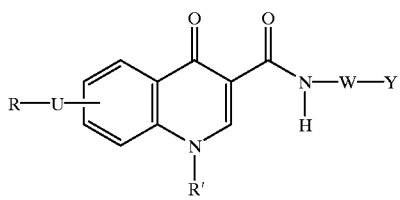

wherein, among the others, U may include —(CH$_2$)$_n$—, —(CH$_2$)$_n$—[O,S,N]—(CH$_2$)$_n$—, or linker groups attached through nitrogen; R may be a nitrogen containing heteroaryl substituent or guanidine substituent; R' may be hydrogen, alkyl(1–4), or phenylalkyl(1–4); W is a C$_{1-3}$ alkyl in which the alkyl group is substituted by either one or two non-hydrogen substituents which may include a halogen substituted phenyl; and Y may be various carboxylate derivatives, sulfonate derivatives, phosphate derivatives and heterocycles, however, may not be hydrogen.

PCT publication, W099/32450 discloses compounds of structure 6

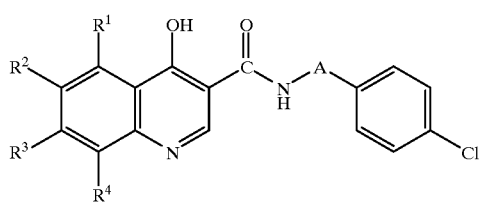

which are useful as antivial agents.

SUMMARY OF THE INVENTION

The present invention provides a compound of formula I

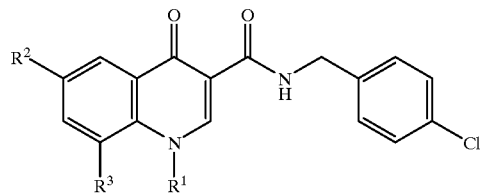

Wherein R$^1$ is C$_{1-7}$ alkyl, optionally substituted by hydroxy or NR$^4$R$^5$; R$^2$ is C$_{1-7}$ alkyl substituted by hydroxy or NR$^4$R$^5$; R$^3$ is H, F or C$_{1-7}$ alkoxy; R$^4$ and R$^5$ together with N are a 5- or 6-membered heterocyclic moiety having 1–3 heteroatoms selected from the group consisting of nitrogen, oxygen and sulfur in which sulfur may be substituted by one (1) or two (2) oxygen atoms; and pharmaceutically acceptable salts thereof.

In another aspect, the present invention also provides:

A pharmaceutical composition which comprises a pharmaceutically acceptable carrier and an effective amount of a compound of formula I, a method of treating and preventing herpesviral infections in a mammal, including human, and a use of a compound of formula I to prepare a medicament for treating and preventing herpesviral infections in a mammal, including human.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix C$_{i-j}$ indicates a moiety of the integer "i" to the integer "j" carbon atoms, inclusive. Thus, for example, (C$_{1-3}$)alkyl refers to alkyl of one to three carbon atoms, inclusive, or methyl, ethyl, propyl and isopropyl, straight and branched forms thereof.

The compounds of the present invention are named according to the IUPAC or CAS nomenclature system.

The term "C$_{1-7}$", "C$_{1-5}$" and "C$_{1-4}$" alkyl refer to an alkyl group having one to seven, one to five and one to four carbon atoms respectively such as, for example, methyl, ethyl, propyl, butyl, pentyl, hexyl, heptyl and their isomeric forms thereof.

A 5- or 6-membered heterocyclic moiety includes thiadiazolyl, thiazolyl, 1,1-dioxo-thiazolyl, 1-oxo-thiazolyl, benzothiazolyl, pyridinyl, imidazolyl, indolyl, pyrrolyl, morpholinyl, thiophenyl and 2-oxo-oxazolyl.

Compounds of the present invention may be in a form of pharmaceutically acceptable salts.

"Pharmaceutically acceptable salts" refers to those salts which possess the biological effectiveness and properties of the parent compound and which are not biologically or otherwise undesirable. Mammal refers to human and animals.

The following Charts A–D describe the preparation of the compounds of formula I of the present invention. All of the starting materials are prepared by procedures described in these charts, by procedures well known to one of ordinary skill in organic chemistry or can be obtained commercially. All of the final compounds of the present invention are prepared by procedures described in these charts or by procedures analogous thereto, which would be well known to one of ordinary skill in organic chemistry. All of the variables used in the charts are as defined below or as in the claims.

In CHART A, structure A-1, ethyl 4-hydroxy-6-iodo-3-quinolinecarboxylate, is prepared by heating 4-iodoaniline with diethyl ethoxymethylene malonate, first at about 150° C., then in refluxing diphenyl ether. Aminolysis of compound A-1 with 4-chlorobenzylamine at about 160° C. provides amide A-2. Palladium and copper mediated coupling of A-2 with propargyl alcohol leads to compound A-3. Alkylation of the pyridone nitrogen is accomplished with potassium carbonate and an optionally substituted alkylhalide, affording the compound of structure A-4. Hydrogenation of the alkyne with hydrogen gas, using platinum catalyst, provides the compound of structure A-5.

CHART A

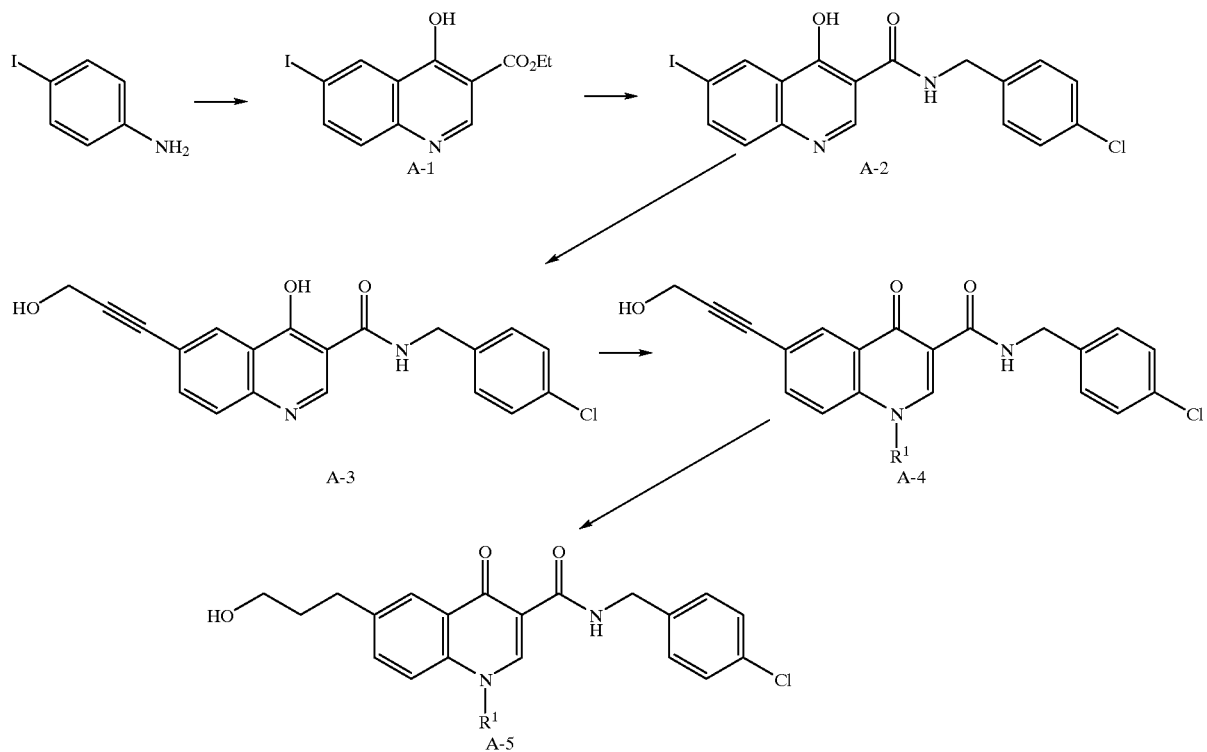

In CHART B, structure B-1, 2-fluoro-5-iodobenzoic acid, is prepared by carbonation of the anion of 4-fluoroiodobenzene. Reaction of B-1 with carbonyldiimidazole, followed by treatment of the resulting acyl imidazolide with ethyl trimethylsilyl malonate and subsequent decarboxylation, affords β-ketoester B-2. The ketoester is converted to quinolinones B-3 by sequential treatment with triethyl orthoformate, an amine, and potassium tert-butoxide. Aminolysis of the ester is accomplished with 4-chlorobenzylamine, giving the compound of structure B-4. Coupling of propargyl alcohol is effected using palladium and copper catalysis, leading to structure B-5. Hydrogenation of the triple bond using hydrogen gas and platinum catalyst provides hydroxypropyl derivatives B-6.

CHART B

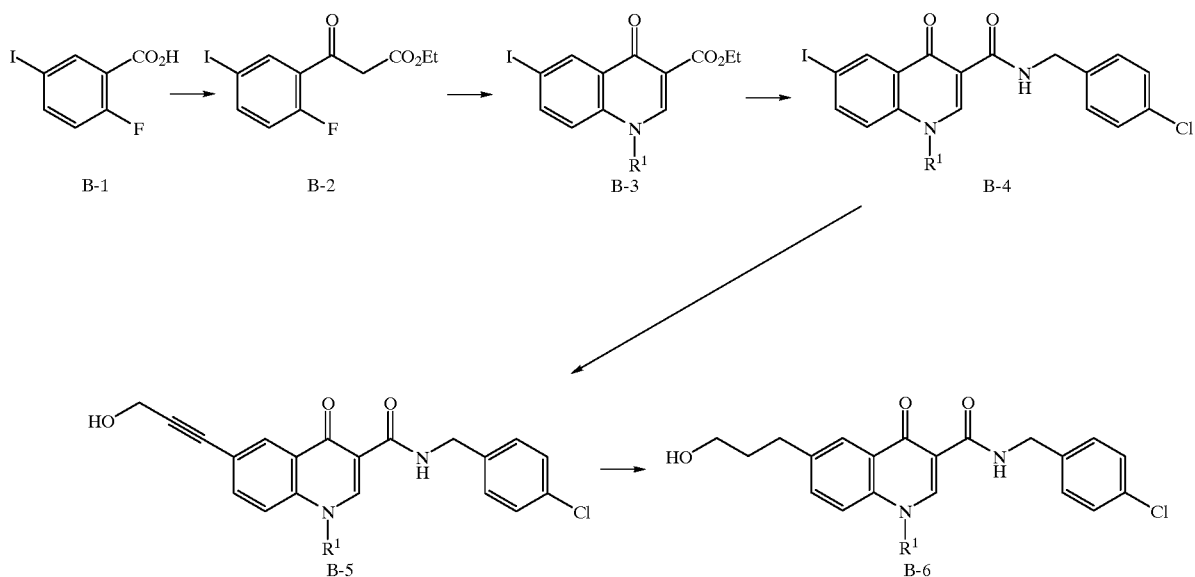

In CHART C, carboxylic acid C-1, 3-methyl-3-(4-nitrophenyl)butanoic acid prepared by carbonylation of the corresponding Grignard, is reduced to the corresponding alcohol with borane. The resulting alcohol C-2 is protected as the benzyl ether and the corresponding nitro functionality is reduced to aniline C-3. Heating C-3 with diethyl ethoxymethylenemalonate followed by thermolysis in refluxing diphenylether affords the 4-hydroxyquinoline C-4. Aminolysis of compound C-4 with 4-chlorobenzylamine at about 190° C. provides amide C-5 which is then alkylated at the pyridone nitrogen with an alkylhalide and potassium carbonate to afford compound C-6. Deprotection of the benzyl ether under hydrogenolysis conditions affords the desired hydroxyalkyl 4-quinolone carboxamide of formula I of the present invention.

CHART C

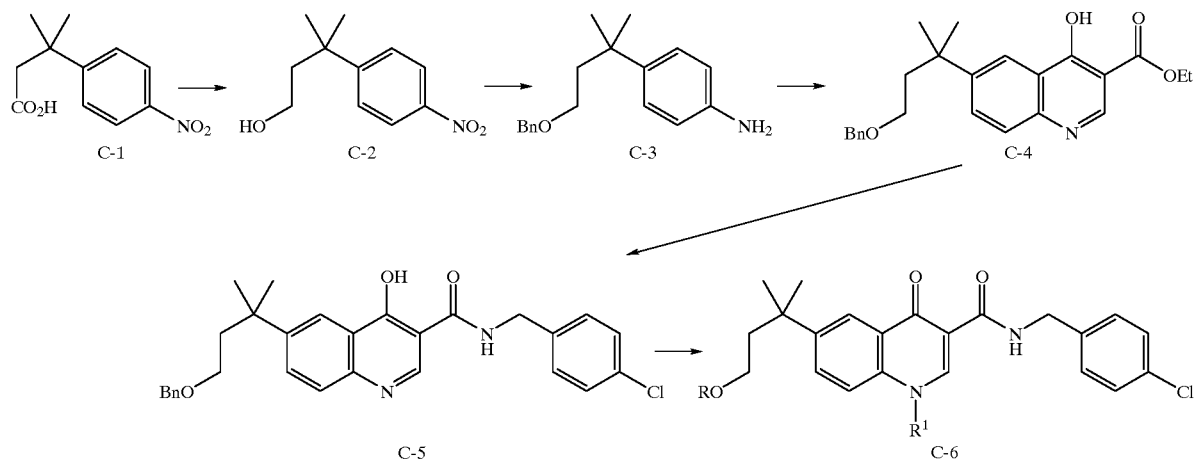

In CHART D, palladium catalyzed carbonylation of the 6-iodo-4-hydroxyquinoline-3-carboxamide A-2 (see CHART A) affords the corresponding ester D-1 which is then reduced with LAH to afford the alcohol D-2. Alkylation of the pyridone nitrogen with alkylhalide and potassium carbonate affords structure D-3. Treatment of D-3 with methanesulfonylchloride followed by displacement with a corresponding primary or secondary amine affords compounds of the structure D-4, wherein $R_4$ and $R_5$ are as defined above.

CHART D

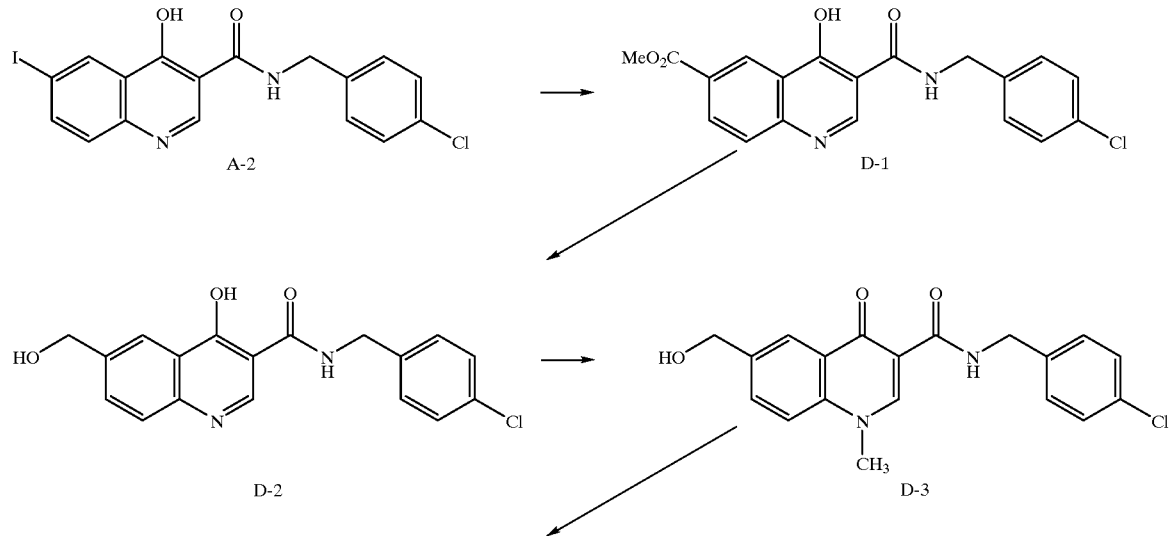

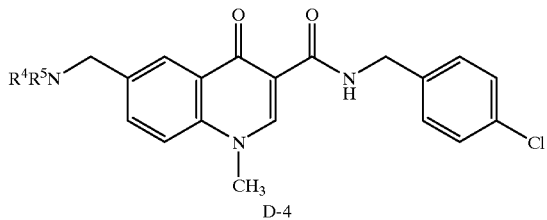

In CHART E, the corresponding compound of Formula D-4 (see CHART D) where $NR_2$ is thiomorpholine is reacted with meta-chloroperbenzoic acid to afford the sulfoxide (E-1) and the sulfone (E-2).

CHART E

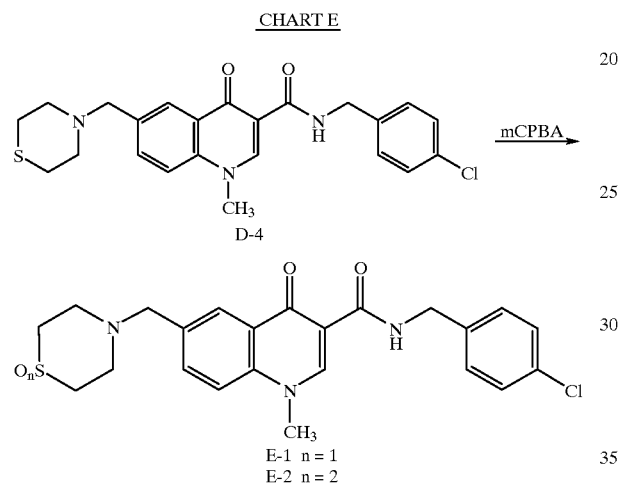

Chart F illustrates a specific method for the preparation of the compound of formula I of the present invention. In CHART F, N-methylaniline F-1 is prepared according to a published procedure (Miocque, M; Vierfond, *J. M. Bull. Soc. Chim. Fr.* 1970, 1901–1907). Compound F-1 is then reacted with ethyl ethoxymethylenemalonate to afford F-2, which is heated in a mixture of Eaton's reagent to afford quinolone F-3. Saponification of F-3 under alkaline conditions affords carboxylic acid F-4. Subsequent coupling of F-4 with 4-chlorobenzylamine mediated by CDI provides F-5. The method is further detailed in Example 3b of the present invention.

CHART F

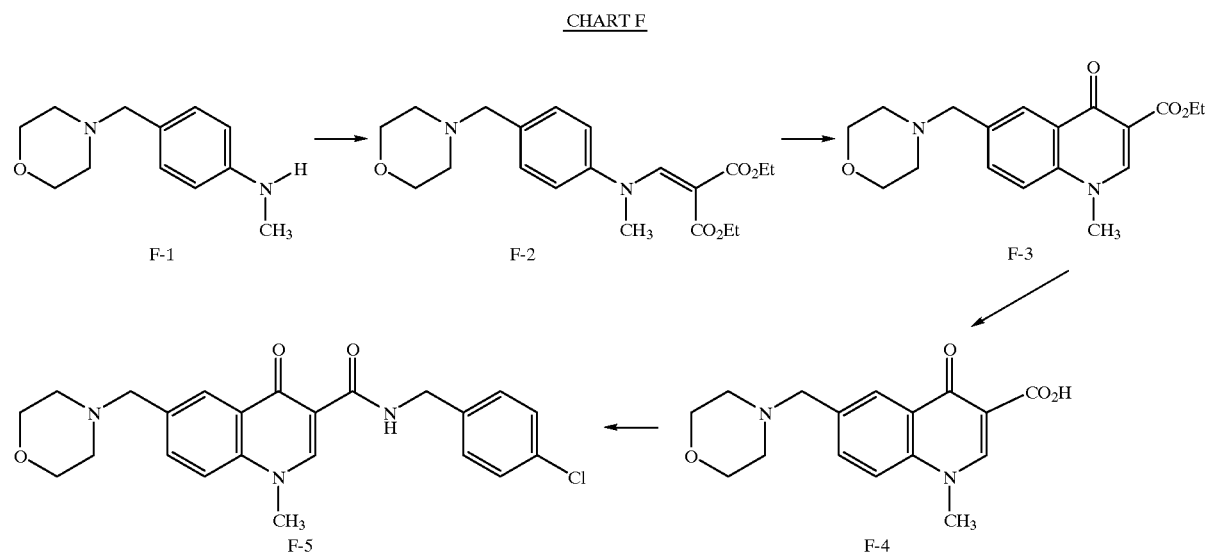

It will be apparent to those skilled in the art that the described synthetic procedures are merely representative in nature and that alternative synthetic processes are known to one of ordinary skill in organic chemistry.

The examples of the present invention are:
(a) N-(4-Chlorobenzyl)-6-(3-hydroxy-1,1-dimethylpropyl)-1-methyl-4-oxo-1,4-dihydro-3-quinolinecarboxamide;
(b) N-(4-Chlorobenzyl)-1-methyl-6-(4-morpholinylmethyl)-4-oxo-1,4-dihydro-3-quinolinecarboxamide;
(c) N-(4-Chlorobenzyl)-1-(2-hydroxyethyl)-6-(3-hydroxypropyl)-4-oxo-1,4-dihydro-3-quinolinecarboxamide;
(d) N-(4-Chlorobenzyl)-6-(3-hydroxypropyl)-1-methyl-4-oxo-1,4-dihydro-3-quinolinecarboxamide;
(e) 1-(tert-Butyl)-N-(4-chlorobenzyl)-6-(3-hydroxypropyl)-4-oxo-1,4-dihydro-3-quinolinecarboxamide;
(f) N-(4-Chlorobenzyl)-6-[(1,1-dioxo-1',4-thiazinan-4-yl)methyl]-1-methyl-4-oxo-1,4-dihydro-3-quinolinecarboxamide;
(g) N-(4-Chlorobenzyl)-1-methyl-4-oxo-6-[(1-oxo-1',4-thiazinan-4-yl)methyl]-1,4-dihydro-3-quinolinecarboxamide;
(h) N-(4-chlorobenzyl)-8-fluoro-1-methyl-6-(4-morpholinylmethyl)-4-oxo-1,4-dihydro-3-quinolinecarboxamide; or a pharmaceutically acceptable salt thereof.

The preferred compounds of the present invention are:
(a) N-(4-Chlorobenzyl)-6-(3-hydroxy-1,1-dimethylpropyl)-1-methyl-4-oxo-1,4-dihydro-3-quinolinecarboxamide;
(b) N-(4-Chlorobenzyl)-1-methyl-6-(4-morpholinylmethyl)-4-oxo-1,4-dihydro-3-quinolinecarboxamide;
(c) N-(4-Chlorobenzyl)-1-(2-hydroxyethyl)-6-(3-hydroxypropyl)-4-oxo-1,4-dihydro-3-quinolinecarboxamide;
(d) N-(4-Chlorobenzyl)-6-(3-hydroxypropyl)-1-methyl-4-oxo-1,4-dihydro-3-quinolinecarboxamide;
(e) N-(4-Chlorobenzyl)-6-[(1,1-dioxo-1',4-thiazinan-4-yl)methyl]-1-methyl-4-oxo-1,4-dihydro-3-quinolinecarboxamide;
(f) N-(4-Chlorobenzyl)-1-methyl-4-oxo-6-[(1-oxo-1',4-thiazinan-4-yl)methyl]-1,4-dihydro-3-quinolinecarboxamide;
(g) N-(4-chlorobenzyl)-8-fluoro-1-methyl-6-(4-morpholinylmethyl)-4-oxo-1,4-dihydro-3-quinolinecarboxamide; or a pharmaceutically acceptable salt thereof.

The more preferred compounds of the present invention are:
(a) N-(4-Chlorobenzyl)-1-methyl-6-(4-morpholinylmethyl)4-oxo-1,4-dihydro-3-quinolinecarboxamide;
(b) N-(4-Chlorobenzyl)-6-(3-hydroxypropyl)-1-methyl-4-oxo-1,4-dihydro-3-quinolinecarboxamide;
(c) N-(4-Chlorobenzyl)-6-[(1,1-dioxo-1',4-thiazinan-4-yl)methyl]-11-methyl-4-oxo-1,4-dihydro-3-quinolinecarboxamide;
(d) N-(4-Chlorobenzyl)-1-methyl-4-oxo-6-[(1-oxo-1',4-thiazinan-4-yl)methyl]-1,4-dihydro-3-quinolinecarboxamide;
(e) N-(4-chlorobenzyl)-8-fluoro-1-methyl-6-(4-morpholinylmethyl)-4-oxo-1,4-dihydro-3-quinolinecarboxamide; or a pharmaceutically acceptable salt thereof.

The most preferred compounds of the present invention is N-(4-Chlorobenzyl)-1-methyl-6-(4-morpholinylmethyl)-4-oxo-1,4-dihydro-3-quinolinecarboxamide, or a pharmaceutically acceptable salt thereof.

Also, there is a specific value for the following compounds as synthetic intermediates in the preparation of the preferred compound of formula I:
(a) diethyl 2-{[methyl-4-(4-morpholinylmethyl)anilino]methylene}malonate;
(b) ethyl 1-methyl-6-(4-morpholinylmethyl)-4-oxo-1,4-dihydro-3-quinolinecarboxylate; and
(c) 1-methyl-6-(4-morpholinylmethyl)-4-oxo-1,4-dihydro-3-quinolinecarboxylic acid.

The compounds of the present invention and pharmaceutically acceptable salts thereof are useful as antiviral agents. Thus, these compounds are useful to combat viral infections in animals, including man. Specifically, these compounds have anti-viral activity against the herpes virus, cytomegalovirus (CMV). These compounds are also active against other herpes viruses, such as the varicella zoster virus, the Epstein-Barr virus, the herpes simplex virus, and the human herpes virus type 8 (HHV-8).

Also, while many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention have shown activity in one or more of the assays described below. All of these assays are indicative of a compound's activity and thus of its use as an anti-viral agent.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C or 37 C $H_2O$ bath and terminated via the addition of 40 μl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37 C, then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of compounds of the present invention in this assay are shown in Tables 1 below. Other viral polymerase assays are performed using procedures similar to those described above.

These compounds of the present invention are administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975), which is hereby incorporated by reference herein.

The compounds of the present invention are administered parenterally (for example, by intravenous, intraperitoneal or intramuscular injection), topically, orally, or rectally, depending on whether the preparation is used to treat internal or external viral infections.

For internal infections, the compositions are administered orally or parenterally at dose levels, calculated as the free base, of about 0.1 to 300 mg/kg, preferably 1.0 to 30 mg/kg of mammal body weight, and are used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to 10%, more preferably about 0.1 to 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

TABLE 1

| | polymerase IC$_{50}$ ($\mu$M) | | |
|---|---|---|---|
| Example No. | HCMV | HSV | VZV |
| 1 | 0.5 | 1.8 | 2.0 |
| 2 | 7.8 | — | — |
| 3 | 0.4 | 0.74 | 0.44 |
| 4 | 0.37 | — | — |
| 5 | 0.48 | 0.32 | 0.41 |
| 6 | 2.8 | — | — |
| 7 | 2.5 | — | — |
| 8 | 2.6 | — | — |
| 9 | 4.7 | — | — |
| 10 | 1.0 | — | — |

The term "—" refers to the data are not determined

The term "—" refers to the data are not determined

The compounds and their preparation of the present invention will be better understood in connection with the following examples, which are intended as an illustration of and not a limitation upon the scope of the invention.

EXAMPLE 1

N-(4-chlorobenzyl)-6-(3-hydroxy-1,1-dimethylpropyl)-1-methyl-4-oxo-1,4-dihydro-3-quinolinecarboxamide

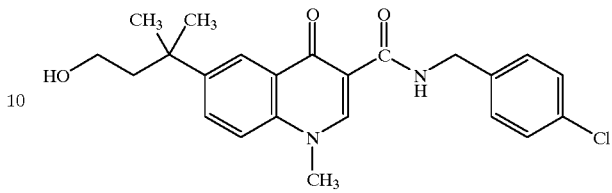

To a suspension of 3-methyl-3-(4-nitrophenyl)butanoic acid (16.2 g) (J. Amer. Chem. Soc. 1981, 103, 7768–7773. and J. Amer. Chem. Soc. 1948, 370–371.) in THF (70 mL) is added 103 mL of a 1.0 M borane/THF solution. The reaction is stirred at room temperature for 18 hours. The reaction is poured into H$_2$O (500 mL). The aqueous layer is saturated with potassium carbonate and extracted with dichloromethane (3×500 mL). The combined organic layers are dried with MgSO$_4$, filtered, and concentrated in vacuo to yield 16.16 g of the alcohol as a yellow solid. The alcohol (9.41 g) is dissolved in THF (100 mL). Sodium hydride (60% oil dispersion; 5.40 g) is added followed by addition of benzyl bromide (16.0 mL). The reaction is stirred at room temperature for 18 hours. The reaction mixture is partitioned between H$_2$O (400 mL) and dichloromethane (400 mL). The aqueous layer is extracted with dichloromethane (2×400 mL). The combined organic layers are washed with brine (400 mL), dried with MgSO$_4$, filtered, and concentrated in vacuo. The resulting yellow oil is purified by column chromatography to yield 8.86 g (64%) of the benzyl protected compound as a yellow oil. This material (8.51 g) is suspended in 1/1 conc. HCl/ethanol (200 mL) and SnCl$_2$.2H$_2$O (19.22 g) is added. The reaction is heated to 70° C. and is stirred for 2 hours. The reaction mixture is cooled to room temperature, and H$_2$O (400 mL) is added. The aqueous layer is adjusted to pH 12 with ammonium hydroxide and then extracted with dichloromethane (2×400 mL). The combined organic layers are dried with MgSO$_4$, filtered, and concentrated in vacuo. The resulting brown oil is purified by column chromatography (dichloromethane; dichloromethane/methanol, 98/2) to yield 1.306 g (17%) of the amine as a yellow oil. This material (1.306 g) is combined with diethylethoxylmethylenemalonate (0.98 mL) and heated to 120° C. for 2 hours. The reaction mixture is purified by column chromatography (dichloromethane; dichloromethane/methanol, 98/2) to yield 2.044 g (96%) of the malonate intermediate as a yellow oil. This material (2.007 g) is dissolved in diphenyl ether (10 mL) and heated to reflux with removal of ethanol via a Dean-Stark trap for 30 min. The reaction is cooled to room temperature and heptane and ethyl acetate are added. The reaction mixture is allowed to stand at room temperature overnight. The resulting precipitate is filtered off and triturated with ethyl acetate to yield the 0.572 g (32%) of the ester as an off-white solid. The ester (0.517 g) and 4-chlorobenzylamine (1.60 mL) are combined and heated to 190° C. for 1 hour. The reaction is cooled to room temperature and ethyl acetate and heptane are added. The mixture is allowed to stand in the freezer for 3 d. The resulting precipitate is filtered off and recrystallized from ethyl acetate/heptane to yield 0.479 g (75%) of the amide as an off-white solid. To a solution of the amnide (0.565 g) in DMF (5 mL) is added potassium carbonate (0.473 g) followed by iodomethane (0.21 mL). The reaction is heated to 90° C. and stirred for 18 hours. The reaction mixture is cooled to room temperature and concentrated in vacuo. The resulting residue is purified by column chromatography (dichloromethane; dichloromethane/methanol 98/2). Fractions homogeneous by TLC are combined and concentrated in vacuo to yield a pale yellow solid which is recrystallized from ethyl acetate/heptane to yield 0.471 g (81 %) of the N-methyl pyridone as a white solid. A solution of the pyridone (0.350 g) in ethanol (50 mL) is hydrogenated over Pd Black (35 mg) for 45 min. The reaction mixture is filtered through a Celite pad and concentrated in vacuo. The resulting yellow solid is recrystallized from ethyl acetate to yield 0.225 g (78%) of the title compound as a pale yellow solid.

Physical characteristics are as follows:

Mp 135–138° C.;

$^1$H NMR (300 MHz, DMSO-d$_6$) δ 10.47, 8.85, 8.26, 7.92, 7.79, 7.42–7.35, 4.57, 4.27, 4.04, 3.20, 1.90, 1.35;

$^{13}$C NMR (75 MHz, DMSO-d$_6$) δ 176.0, 165.0, 149.0, 146.7, 139.1, 138.5, 131.9, 131.7, 129.6, 128.9, 128.8, 127.8, 126.9, 122.3, 118.0, 110.8, 58.2, 46.6, 41.9, 41.6, 37.0, 29.5;

MS (ESI+) for m/z 413 (M+H)$^+$;

IR (drift) 2919, 1916, 1659, 1612, 1555, 1533, 1494, 1431, 1360, 1352, 1085, 813, 806, 797, 682 cm$^{-1}$.

Anal. Found (corrected for 0.17% H$_2$O): C, 66.39; H, 6.16; N, 6.65; Cl, 8.39.

PREPARATION 1

N-[(4-Chlorophenyl)methyl]-4-hydroxy-6-iodo-3-quinoline-carboxamide

4-Iodoaniline (8.60 g) and diethyl ethoxymethylenemalonate (7.90 mL) are heated at 130° C. for 1 hour. The reaction is cooled to room temperature and 60 mL diphenyl ether is added. The solution is heated at 250° C. for 1.5 hours with removal of ethanol by a Dean-Stark trap. The reaction is cooled to room temperature and the resulting solid is filtered, washed with hexanes, and dried to yield 11.20 g of ethyl 4-hydroxy-6-iodoquinoline-3-carboxylate. A mixture of this ester (0.58 g) and 4-chlorobenzylamine (4.0 mL) are heated at 180° C. for 1.5 hours. The reaction is cooled and poured into 50 mL diethyl ether. The resulting solid is filtered, triturated in ethyl acetate, and filtered again to give the desired product (0.50 g).

Physical characteristics are as follows:

Mp 297–299° C.;

$^1$H NMR (300 MHz, DMSO-d$_6$) 12.71, 10.27, 8.76, 8.50, 8.02, 7.50, 7.38, 7.33, 4.52;

IR (mull) 3151, 3078, 3039, 1631, 1610, 1572, 1563, 1545, 1527, 1512, 1491, 1433, 1351, 1303, 799 cm.-$^1$;

MS (ES) 438.9 (M+H), 460.9 (M+Na), 436.9 (M–H). Anal. Found: C, 46.61; H, 2.81; N, 6.34; Cl, 8.19.

PREPARATION 2

Methyl 3-{[(4-chlorobenzyl)amino]carbonyl}-4-hydroxy-6-quinolinecarboxylate

A solution of N-(4-chlorobenzyl)-4-hydroxy-6-iodo-3-quinolinecarboxamide from Preparation No. 1 (30.0 g), Et$_3$N (19.1 mL), MeOH (110.6 mL), Pd(OAc)$_2$ (431 mg), and 1,3-bis (diphenylphosphino) propane (791.9 mg) in 375 mL anhydrous DMF is stirred at room temperature until everything dissolves. CO(g) is slowly bubbled through for 2 days and the reaction is maintained at 70° C. The reaction is cooled to room temperature. The product is precipitated by adding 160 ML 1N HCl to the reaction mixture. An orange solid precipitates and is collected. The solid is triturated with EtOAc, filtered, and washed with CH$_2$Cl$_2$ to afford 23.8 g (93%) of the title compound as an off-white solid.

Physical characteristics are as follows:

Mp 290–292° C.;

$^1$H NMR (300 MHz, DMSO) δ 12.96, 10.26, 8.83, 8.25, 7.80, 7.39, 4.57, 3.9;

IR (drift) 3222, 1724, 1646, 1619, 1574, 1544, 1512, 1489, 1404, 1359, 1288, 1277, 1242, 1210, 738 cm$^{-1}$;

HRMS (FAB) Found 371.0794. Anal. Found: C, 61.54; H, 3.88; N, 7.51.

PREPARATION 3

N-(4-Chlorobenzyl)-4-hydroxy-6-(hydroxymethyl)-3-quinolinecarboxamide.

In a flame-dried 1L 3-necked roundbottom, methyl 3-{ [(4-chlorobenzyl)amino]-carbonyl}-4-hydroxy-6-quinolinecarboxylate from Preparation No. 2 (3.0 g) is dissolved in 700 mL distilled THF. The suspension is heated to 67° C. to solubilize the starting material. The reaction is allowed to cool to room temperature and then cooled in an ice bath to 10° C. Lithium aluminum hydride (552.2 mg) is added in one portion. The reaction is stirred at 25° C. and monitored by mass spectroscopy for conversion to desired product. The reaction is quenched by adding 2 mL H$_2$O, 2 mL 15% NaOH, and 2 mL H$_2$O to the reaction mixture. The reaction mixture is filtered to remove the aluminum salt that had precipitated. The filtrate is condensed to obtain a yellow-green residue. The residue is adsorbed onto silica and chromatographed eluting with 2% MeOH in CH$_2$Cl$_2$ (1L), 3% MeOH in CH$_2$Cl$_2$ (2L), 4% MeOH in CH$_2$Cl$_2$ (2L), 5% MeOH in CH$_2$Cl$_2$ (1L), 6% MeOH in CH$_2$Cl$_2$ (1L), and 7% MeOH in CH$_2$Cl$_2$ (2L). The desired product elutes with 4–7% MeOH in CH$_2$Cl$_2$. Fractions homogenous by TLC are condensed to yield 1.85 g (67%) of the title compound as yellow crystals.

Physical characteristics are as follows:

Mp 288–289° C.;

$^1$H NMR (300 MHz, DMSO) δ 12.71, 10.48, 8.74, 8.21, 7.71, 7.66, 7.39, 5.38, 4.63, 4.56;

MS (ESI) 343.3 (M+H)$^+$, 341.3 (M–H)$^-$.

EXAMPLE 2

N-(4-Chlorobenzyl)-6-(hydroxymethyl)-1-methyl-4-oxo-1,4-dihydro-3-quinolinecarboxamide

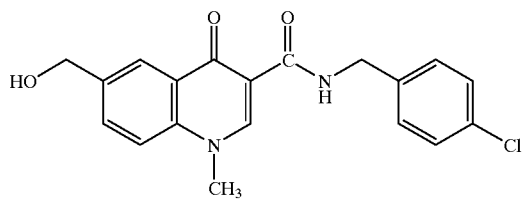

A solution of N-(4-chlorobenzyl)-4-hydroxy-6-(hydroxymethyl)-3-quinolinecarboxamide from Preparation No. 3 (300 mg,), K$_2$CO$_3$ (485.1 mg), and CH$_3$I (0.11 mL) in 4 mL anhydrous DMF is heated at 90° C. for 3 hours. The reaction is cooled to room temperature and diluted with $H_2O$ to dissolve any salts and precipitate the product. The crude product is adsorbed onto silica and chromatographed eluting with 3% MeOH in $CH_2Cl_2$. Fractions homogenous by TLC are combined and condensed to afford 154.2 mg (49%) of the title compound as a white solid.

Physical characteristics are as follows:

Mp 168–170° C.;

$^1$H NMR (300 MHz, DMSO) δ 10.45, 8.87, 8.30, 7.80, 7.38, 5.42, 4.66, 4.57, 4.02;

MS (ESI) 357.2 $(M+H)^+$, 355.3 $(M-H)^-$.

Anal. Found: C, 63.73; H, 4.62; N, 7.70.

EXAMPLE 3a

N-(4-Chlorobenzyl)-1-methyl-6-(4-morpholinylmethyl)-4-oxo-1,4-dihydro-3-quinolinecarboxamide.

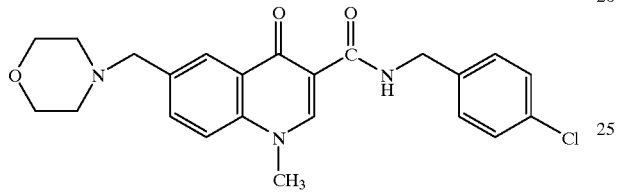

A solution of N-(4-chlorobenzyl)-6-(hydroxymethyl)-1-methyl-4-oxo-1,4-dihydro-3-quinolinecarboxamide from the product of Example 2 (140 mg), collidine (0.061 mL), and DMAP (8.1 mg) in 6.7 mL anhydrous DMF is cooled to 0° C. Methanesulfonyl chloride (0.12 mL) is added dropwise. The reaction is stirred at room temperature for approx. 2–3 hrs. Morpholine (0.34 mL) is added. The product is precipitated by addition of $H_2O$. The crude product is adsorbed onto silica and chromatographed eluting with 2% MeOH in $CH_2Cl_2$. Fractions homogenous by TLC are combined and condensed to afford 70.1 mg (42%) of the title compound as a white solid.

Physical characteristics are as follows:

Mp 188–190° C.;

$^1$H NMR (300 MHz, DMSO) δ 10.43, 8.87, 8.25, 7.81, 7.38, 4.56, 4.02, 3.63, 3.58, 2.38;

IR(drift) 1654, 1606, 1568, 1554, 1501, 1364, 1348, 1342, 1316, 1134, 1111, 1005, 825, 808, 800 cm$^{-1}$;

MS (ESI) 426.3 $(M+H)^+$, 424.2 $(M-H)^-$. Anal. Found: C, 64.61; H, 5.54; N, 9.73.

PREPARATION 4

N-(4-Chlorobenzyl)-4-hydroxy-6-(3-hydroxy-1-propynyl)-3-quinolinecarboxamide.

To a mixture of N-(4-chlorobenzyl)-4-hydroxy-6-iodo-3-quinolinecarboxamide from Preparation No. 1 (0.494 g) in $Et_2NH$ (12.9 mL) is added CuI (10.8 mg) and $(Ph_3P)_2PdCl_2$ (39.7 mg). DMF (2 mL) is added to solubilize the reactants. To this solution is added propargyl alcohol (0.066 mL) and the reaction is stirred at room temperature for 2 days. The reaction mixture is concentrated to remove $Et_2NH$. The resulting residue is partitioned between $CH_2Cl_2$ (3×) and $H_2O$. A brown solid precipitated from the $CH_2Cl_2$ layer is filtered and collected to obtain pure product as indicated by NMR. The organic layers are combined, dried over $Na_2SO_4$, and concentrated to obtain a brown residue. The residue is placed under high vac to remove residual DMF. The residue is adsorbed onto silica and chromatographed eluting with 2% MeOH in $CH_2Cl_2$ and 3% MeOH in $CH_2Cl_2$. Fractions homogenous by TLC are combined, condensed and recrystallized with EtOAc/hexanes to obtain a creme solid. The two crops yielded 325.4 mg (79%) of the desired product as a tan solid.

Physical characteristics are as follows:

MP 248–250 C;

$^1$H NMR (300 MHz, DMSO) 12.85, 10.31, 8.78, 8.22, 7.78, 7.70, 7.38, 5.39, 4.55, 4.33;

IR (drift) 3161, 3073, 3003, 2960, 2914, 1656, 1614, 1557, 1517, 1487, 1299, 1014, 1006, 826, 805 cm$^{-1}$;

MS (ESI) 367.0 $(M+H)^+$, 365.1 $(M-H)^-$. Anal. Found: C, 65.23; H, 4.24; N, 7.60.

PREPARATION 5

N-(4-Chlorobenzyl)-1-(2-hydroxyethyl)-6-(3-hydroxy-1-propynyl)-4-oxo-1,4-dihydro-3-quinolinecarboxamide.

To a flask containing N-(4-chlorobenzyl)-4-hydroxy-6-(3-hydroxy-1-propynyl)-3-quinolinecarboxamide from Preparation No. 4 (0.37 g) is added potassium carbonate (2.75 g) and bromoethanol (0.71 mL). The flask is tightly capped and heated to 100° C. After 4 hours the reaction is cooled to room temperature and partioned between dichloromethane containing methanol and water. The organic layer is washed with two additional portions of water, brine, dried and concentrated under reduced pressure. The residue is adsorbed onto silica and chromatographed on silica eluting with 2% to 10% methanol in dichloromethane to afford 0.09 g of the title compound as a white solid.

Physical characteristics are as follows:

$^1$H NMR (300 MHz, DMSO-d$_6$) 10.2, 8.8, 8.3, 7.9, 7.8, 7.4, 5.4, 5.0, 4.5, 4.3, 3.7 ppm;

MS (ESI) m/z 433 $(M+Na^+)$.

EXAMPLE 3b

Alternatively, the compound of EXAMPLE 3a can be preparaed as follows:

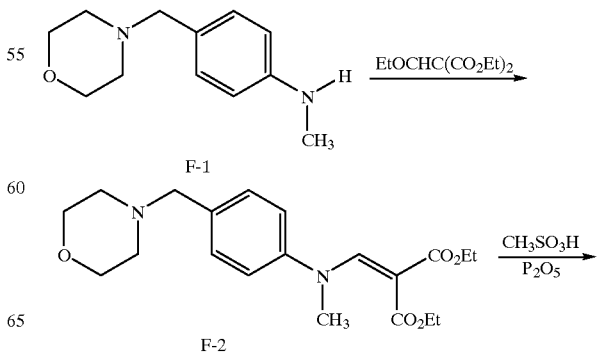

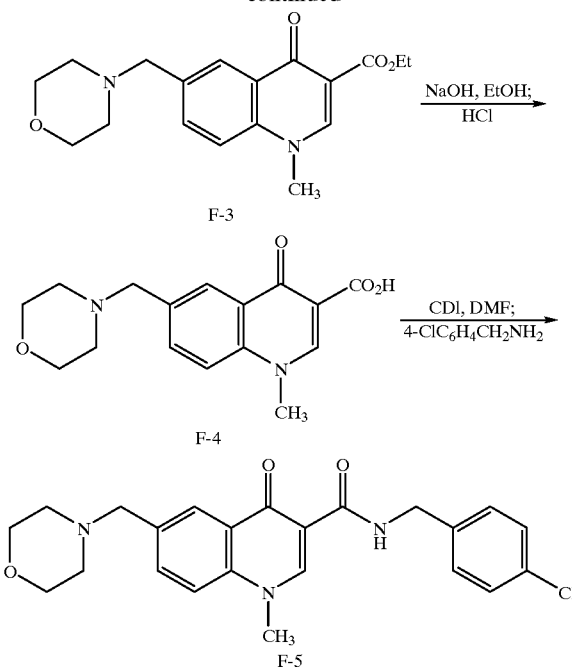

PREPARATION OF F-2

Diethyl 2-{[methyl-4-(4-morpholinylmethyl)anilino] methylene } malonate

A three liter three-neck flask is charged with F-1 (Miocque, M; Vierfond, J. M. *Bull. Soc. Chim.* Fr. 1970, 1901–1907), N-(4-methylaminobenzyl)-morpholine (957 g) and diethyl ethoxymethylenemalonate (938 ml) rinsing with ethanol as needed. The solution is heated slowly to about 108° C. with atmospheric distillation of ethanol by-product. Distillation is continued until <5 % morpholine starting material remained as determined by TLC (silica gel GF; 5 % methanol/methylene chloride). The solution is cooled to room temperature and the residual ethanol is removed by vacuum distillation and toluene azeotrope. High vacuum drying afforded 1778 g (102 % yield) of the title compound F-2 as yellow oil.

$^1$H NMR (400 MHz CDCl3) ppm 7.76 (s, 1H), 7.20 (m, 4H), 4.15 (m, 4H), 3.70 (m, 4H), 3.50 (s, 2H), 3.33 (s, 3H), 2.45 (m, 4H) and 1.30 (m, 6H).

$^{13}$C NMR (100 MHz CDCl3) ppm 167.19, 167.03, 148.72, 145.90, 135.63, 130.12, 121.69, 98.23, 67.00, 62.66, 60.89, 60.27, 53.60, 40.26, 14.41, and 14.15.

PREPARATION OF F-3

Ethyl 1-methyl-6-(4-morpholinylmethyl)-4-oxo-1,4-dihydro-3-quinolinecarboxylate.

A 12 liter three-neck flask is charged with phosphorus pentoxide (294 g) and methanesulfonic acid (1792 ml). The mixture is heated to 50° C. with stirring to dissolve the phosphorus pentoxide. The acid solution is cooled to room temperature and a solution of F-2 (780.5 g) in toluene (780.5 ml) is added over 2 hours maintaining the temperature at <60° C. After 1 hr at 48–59° C. the reaction is complete as determined by TLC (silica gel GF; 5 % methanol/ methylene chloride). The solution is cooled to 0–5° C. and water (780 ml) is added slowly at <36° C. The pH of the slurry is adjusted to 9.5 to 10.5 by addition of 10 M aqueous sodium hydroxide (3365 ml) at <36° C. Water (9330 ml) and methylene chloride (6900 ml) are then added and the product is extracted into the organic layer. The aqueous layer is extracted with methylene chloride (3500 ml). The combined organic layers are washed with water (4000 ml). Removal of the solvent by distillation provided 665 g (97 % yield) of the title compound F-3 as pale yellow crystals.

1H NMR (400 MHz CDCl3) ppm 8.42 (m, 2H), 7.40 (m, 1H), 7.39 (m, 1H), 4.38 (q, 2H), 3.88 (s, 3H), 3.68 (m, 4H), 3.62 (s, 2H), 2.47 (m, 4H), and 1.42 (t, 3H) 13C NMR (100 MHz CDCl3) ppm 174.36, 165.85, 149.47, 138.98, 135.38, 133.58, 128.70, 127.96, 115.80, 111.01, 66.97, 62.53, 60.84, 53.54, 41.35, and 14.44.

PREPARATION OF F-4

1-methyl-6-(4-morpholinylmethyl)-4-oxo-1,4-dihydro-3-quinolinecarboxylic acid.

A 22 liter three-neck flask is charged with F-3 (755 g), ethanol (3776 ml), water (3776 ml), and 50 % sodium hydroxide (831 ml). With stirring under nitrogen the mixture is heated to reflux and maintained until the F-3 is consumed as determined by TLC (silica gel GF; 15 % methanol in methylene chloride, uv). After 1 hr at reflux the reaction is complete. The ethanol is removed by vacuum distillation and the aqueous layer is extracted with methyl t-butyl ether (7550 ml). The pH of the aqueous layer is then lowered to 3.8–4.2 using 6 M hydrochloric acid (2700 ml). The resulting colorless slurry is cooled to 0 to 3° C. with stirring. The title compound F-4 is filtered on a coarse sintered glass funnel and washed with 0 to 3° C. water (375 ml). The product is dried at 40° C. in the vacuum over with nitrogen sweep until <0.3 % water remained. The yield of F-4 as colorless crystals is 599 g (86.6 % yield). The residual water is 0.245 wt %.

$^1$H NMR (400 MHz D2O) ppm 8.70 (s, 1H), 8.39 (s, 1H), 8.11 (m, 1H), 8.02 (m, 1H), 4.83 (s, 3H), 4.66 (s, 2H), 4.05 (m, 4H), and 3.49 (m, 4H). $^{13}$C NMR (100 MHz D2O) ppm 178.06, 168.84, 150.95, 141.26, 137.44, 129.16, 127.42, 125.39, 119.65, 107.47, 64.09, 59.89, 51.85, and 42.64.

PREPARATIN OF F-5

N-(4-Chlorobenzyl)-1-methyl-6-(4-morpholinylmethyl)-4-oxo-1,4-dihydro-3-quinolinecarboxamide.

A 22 liter three-neck flask is charged with compound F-4, (827 g), 1,1'-carbonyldiimidazole (CDI) (443 g), and dimethyl formamide (4960 ml). With stirring under nitrogen the mixture is heated slowly to 60 to 70° C. The solids gradually dissolved as carbon dioxide is steadily evolved. After adding two additional 22 g portions of CDI over about 4 hr, the starting material is consumed as determnined by TLC (silica gel GF; 6 % methanol in methylene chloride; uv). As the product of Preparation of F-4 reacted a tan solution is produced, which eventually became a slurry as the acyl imidazolide crystallized. To the slurry is added 4-chlorobenzylamine (333 ml) over 11 min with evolution of heat (64 to 75° C.). Dissolution of the imidazolide is followed by crystallization of the product. Stirring is continued at 64 to 80° C. until complete as determined by TLC (silica gel GF; 6 % methanol in methylene chloride; uv). An additional 16.7 ml of 4-chlorobenzylamine are added to complete the reaction. On completion, the slurry is cooled to 25° C. and 0–5° C. water is added (4600 ml). The mixture is cooled to 0–3° C. and filtered on a coarse sintered glass funnel. The cake is ished with 0–3° C. water (2550 ml) and dried in the vacuum oven at 40° C. with a nitrogen sweep. The yield of crude title compound as pale yellow crystals is 947 g (81.3 % yield). The purity by HPLC assay is 97.4 area %. The crude title compound is recrystallized from hot ethanol as needed.

$^1$H NMR (400 MHz CDCl3) ppm 10.46 (br s, 1H), 8.77 (s, 1H), 8.41 (s, 1H), 7.80 (m, 1H), 7.49 (m, 1H), 7.30 (m, 4H), 4.64 (d, 2H), 3.95 (s, 3H), 3.70 (m, 4H), 3.64 (s, 2H), and 2.45 (m, 4H).

$^{13}$C NMR (100 MHz CDCl3) ppm 176.62, 165.07, 148.20, 139.08, 137.40, 135.64, 133.94, 132.74, 128.92, 128.60, 127.44, 127.15, 115.99, 111.71, 66.90, 62.50, 53.51, 42.52, and 41.47.

EXAMPLE 4

N-(4-Chlorobenzyl)-1-(2-hydroxyethyl)-6-(3-hydroxypropyl)-4-oxo-1,4-dihydro-3-quinolinecarboxamide

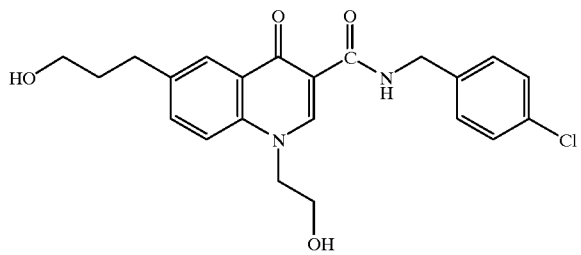

To a solution of N-(4-chlorobenzyl)-1-(2-hydroxyethyl)-6-(3-hydroxy-1-propynyl)-4-oxo-1,4-dihydro-3-quinolinecarboxamide from Preparation No. 5 (0.20 g) in a small amount of THF:methanol is added platinuim oxide (0.01 g). The mixture is placed under an atmosphere of hydrogen. After 2 hours, the mixture is filtered through Celite with THF:methanol washes. The filtrate is concentrated under reduced pressure. The residue is adsorbed onto silica and chromatographed on silica eluting with 4% to 16% methanol in dichloromethane. The product-containing fractions are concentrated under reduced pressure to afford 0.14 g of the title compound as a white solid.

Physical characteristics are as follows:
$^1$H NMR (300 MHz, DMSO-d$_6$) 10.5, 8.7, 8.1, 7.8, 7.7, 7.4, 5.0, 4.5, 3.7, 3.4, 2.7, 1.7;
MS (ESI) m/z 415 (M+H$^+$).

PREPARATION 6

N-(4-Chlorobenzyl)-6-(3-hydroxy-1-propynyl)-1-methyl-4-oxo-1,4-dihydro-3-quinolinecarboxamide.

A suspension of 6.90 g of N-(4-chlorobenzyl)-4-hydroxy-6-(3-hydroxy-1-propynyl)-3-quinolinecarboxamide from Preparation No. 4, 10.4 g of potassium carbonate, and 2.3 mL of methyl iodide in 40 mL of DMF is stirred at 90° C. for 4 hours, then cooled and diluted with 350 mL of water. The resulting solid is filtered, washed well with water, and dried under vacuum. Flash chromatography of the solid on silica using 3–5% methanol in dichloromethane provides 6.02 g of the title compound as a solid.

Physical properties as follows:
$^1$H NMR (CDCl$_3$+CD$_3$OD) δ 4.03, 4.45, 4.6, 7.3, 7.6, 7.8, 8.5, 8.8 ppm; HRMS 381.1006

EXAMPLE 5

N-(4-Chlorobenzyl)-6-(3-hydroxypropyl)-1-methyl-4-oxo-1,4-dihydro-3-quinolinecarboxamide

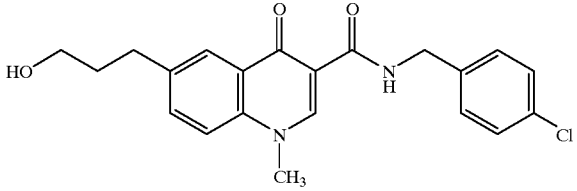

A mixture of 0.50 g of N-(4-chlorobenzyl)-6-(3-hydroxy-1-propynyl)-1-methyl-5 4-oxo-1,4-dihydro-3-quinolinecarboxamide from Preparation No. 6 and 50 mg of 5% platinum on carbon catalyst in 20 mL of 1:1 THF-methanol is stirred under 1 atm hydrogen for 3 hours, then filtered through diatomaceous earth. The filtrate is concentrated under reduced pressure and the residual solid flash chromatographed on silica gel using 4–5% methanol in dichloromethane to afford 0.45 g of the title compound as a yellow solid. Further purification is achieved by recrystallization of the solid from 15 mL of acetonitrile.

Physical properties as follows:
$^1$H NMR (CDCl$_3$+CD$_3$OD) δ 1.9, 2.9, 3.6, 4.0, 4.6, 7.3, 7.5, 7.7, 8.3, 8.8 ppm; HRMS 385.1310.

PREPARATION 7

2-Fluoro-5-iodobenzoic acid

To an argon-covered, stirred solution of 16.8 mL of diisopropylethylamine in 200 mL of THF, cooled at −78° C., is added dropwise 67 mL of a 1.6 M solution of butyllithium in hexane. The solution is allowed to warm to 0° C. and then recooled to −78° C. To this solution is added dropwise 11.5 mL of 4-fluoroiodobenzene in 10 mL of THF. The solution is stirred for 90 min at −78° C, then cannulated rapidly onto a Dry Ice-ether slurry. The mixture is allowed to warm to room temperature, then extracted with 300 mL of 0.3 M NaOH. The aqueous phase is chilled in ice and acidified with 40 mL of 6N HCl. The precipitate is extracted with two portions of ether, and the organic phase dried (MgSO$_4$) and concentrated under reduced pressure. Recrystallization of the residue with ethyl acetate-hexane provides 19.57 g of the title compound as white needles. A second crop of 3.78 g is obtained by recrystallization of the mother liquor residue.

Physical properties as follows:
$^1$H NMR (CDCl$_3$) δ 6.97, 7.88, 8.33 ppm. Anal found: C, 31.57; H, 1.59.

PREPARATION 8

Ethyl 3-(2-fluoro-5-iodophenyl)-3-oxopropanoate

To a stirred solution of 5.32 g of 2-fluoro-5-iodobenzoic acid from Preparation No. 7 in 20 mL of THF, under argon, is added 3.9 g of carbonyldiimidazole. In a separate flask, 2.8 mL of chlorotrimethylsilane is added to a mixture of 3.74 g of potassium ethyl malonate in 20 mL of acetonitrile. The mixture is stirred under argon for 18 h, then cooled to 0° C. for the dropwise addition of 6.6 mL of DBU. The mixture is stirred for 3 h at 0° C., then the solution of acyl imidazolide prepared above is added via cannula. After 2 hours, the mixture is partitioned between ether and excess dilute HCl, and the organic phase is washed with dilute HCl and brine and dried (MgSO$_4$). Removal of the solvent under reduced pressure left a colorless oil, which is flash chromatographed on silica using 10% ethyl acetate in hexane to provide 5.07 g of the title compound as dense pinkish prisms.

Physical properties as follows:
$^1$H NMR (CDCl$_3$) δ 1.34, 4.27, 5.82, 6.89, 7.7, 8.2 ppm; IR 1624, 1485, 1419, 1245, 1193, 1070, 1028, 813 cm$^{-1}$.

PREPARATION 9

Ethyl 1-(tert-butyl)-6-iodo-4-oxo-1,4-dihydro-3-quinolinecarboxylate.

A solution of 2.36 g of ethyl 3-(2-fluoro-5-iodophenyl)-3-oxopropanoate from Preparation No. 8, 2.0 mL of triethyl orthoformate, and 15 mL of acetic anhydride is refluxed under argon for 2 hours, then the solvents are distilled off under reduced pressure. To the residual oil is added 10 mL of dry tert-butanol and 0.74 mL of tert-butylamine, and the solution is stirred at 80° C. for 2 hours. Potassium tert-butoxide (0.87 g) is then added, and stirring continued at 80° C. under argon for 18 hours. The mixture is then cooled and partitioned between dilute HCl and chloroform-methanol. The organic phase is dried (MgSO$_4$) and concentrated under reduced pressure. Flash chromatography of the residue on silica using 2–4% methanol in dichloromethane provides 1.32 g of the title compound as an off-white solid.

Physical properties as follows:
$^1$H NMR (CDCl$_3$) δ 1.42, 1.87, 4.4, 7.7, 7.9, 8.9 ppm; HRMS 400.0414. Anal. Found: C, 48.05; H, 4.50; N, 3.52.

PREPARATION 10

1-(tert-Butyl)-N-(4-chlorobenzyl)-6-iodo-4-oxo-1,4-dihydro-3-quinolinecarboxamide.

A slurry of 1.11 g of ethyl 1-(tert-butyl)-6-iodo-4-oxo-1,4-dihydro-3-quinolinecarboxylate from Preparation No. 9 in 2.0 g of 4-chlorobenzylamine is heated under argon at 160° C. for 18 hours, then cooled to room temperature and triturated with 1N HCl. The solid is filtered, washed well with water, and dried under vacuum. Flash chromatography using 20% ethyl acetate in dichloromethane provides 1.22 g of the title compound as a white solid.

Physical properties as follows:
$^1$H NMR (CDCl$_3$) δ 1.89, 4.6, 7.3, 7.7, 7.9, 8.9, 9.22, 10.4 ppm; IR 1664, 1536, 1468, 1342, 1180cm$^{-1}$.
Anal. Found: C, 51.27; H, 4.19; N, 5.62.

PREPARATION 11

1-(tert-Butyl)-N-(4-chlorobenzyl)-6-(3-hydroxy-1-propynyl)-4-oxo-1,4-dihydro-3-quinolinecarboxamide To a stirred slurry of 1.15 g of 1-(tert-butyl)-N-(4-chlorobenzyl)-6-iodo-4-oxo-1,4-dihydro-3-quinolinecarboxamide from Preparation No. 10, 156 mg of copper (I) iodide, and 66 mg of dichlorobis (triphenylphosphine)palladium (II) in 23 mL of diethylamine, under argon, is added 0.16 mL of propargyl alcohol. The mixture is stirred for 18 hour at room temperature, then concentrated under reduced pressure. The residue is partitioned between water and chloroform-methanol, and the organic phase dried (MgSO$_4$) and concentrated under reduced pressure. Flash chromatography of the residue on silica using 2–4% methanol in dichloromethane affords 977 mg of tan solid. Recrystallization from ethanol provides 850 mg of the title compound as a beige solid.

Physical properties as follows:
$^1$H NMR (CDCl$_3$) δ 1.92, 4.47, 4.6, 7.3, 7.7, 8.0, 8.5, 9.19, 10.5 ppm; HRMS 423.1466.
Anal. Found: C, 67.74; H, 5.53; N, 6.61.

EXAMPLE 6

1-(tert-Butyl)-N-(4-chlorobenzyl)-6-(3-hydroxypropyl)-4-oxo-1,4-dihydro-3-quinolinecarboxamide.

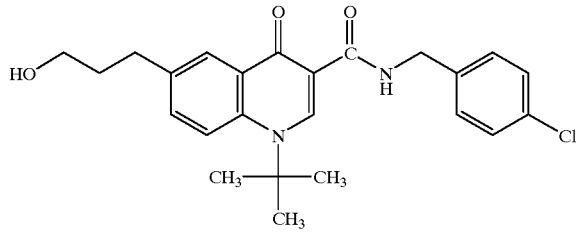

A mixture of 303 mg of 1-(tert-butyl)-N-(4-chlorobenzyl)-6-(3-hydroxy-1-propynyl)-4-oxo-1,4-dihydro-3-quinolinecarboxamide from Preparation No. 11 and 15 mg of platinum oxide in 10 mL of 1:1 THF-methanol is stirred under 1 atm of hydrogen gas for 3 h, then filtered through diatomaceous earth and concentrated under reduced pressure. The mixture was purified by flash chromatography on silica using 2–3% methanol in dichloromethane to afford 294 mg of the title compound.

Physical properties as follows:
$^1$H NMR (CDCl$_3$) δ 1.89, 1.9, 2.9, 3.7, 4.6, 7.3, 7.5, 7.9, 8.4, 9.21, 10.6 ppm; IR 1658, 1596, 1548, 1484, 1349, 1184, 810, 731 cm$^{-1}$; HRMS 427.1762

EXAMPLE 7

N-(4-Chlorobenzyl)-1-methyl-4-oxo-6-(4-thiomorpholinyl-methyl)-1,4-dihydro-3-quinolinecarboxamide.

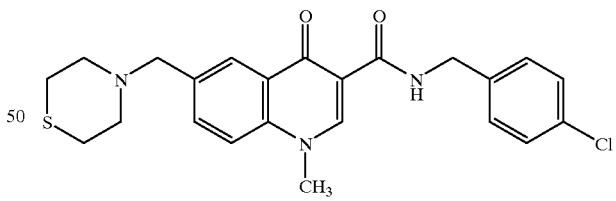

Methanesulfonyl chloride (0.193 mL) is added to a solution of N-(4-chloro-benzyl)-6-(hydroxymethyl)-1-methyl-4-oxo-1,4-dihydro-3-quinolinecarboxamide (357 mg) from Example No. 2, DMAP (20 mg), and 2,4,6-collidine (0.33 mL) in anhydrous DMF (20 mL). The mixture is stirred at room temperate for 2 h, and poured into water (60 mL). The resulting percipitate is filtered, washed with water (20 mL), and recrystallized from acetonitrile to afford 0.328 g (74%) of the title compound as a white solid.

Physical characteristics are as follows:
Mp 215–219° C.; $^1$H NMR (DMSO-d$_6$) δ 10.42, 8.87, 8.23, 7.80, 7.42–7.34, 4.56, 4.02, 3.66, 2.62; $^{13}$C NMR (DMSO-d$_6$) δ 175.4, 164.4, 148.7, 139.0, 138.7, 135.3, 133.7, 131.3, 129.1, 128.3, 126.7, 125.6, 117.6, 110.5, 61.8, 54.3, 41.4, 41.2, 27.2; IR (drift) 2915, 1655, 1605, 1574, 1551, 1502, 1364, 1339, 1316, 1132, 826, 808, 801, 726, 661 cm$^{-1}$; MS (ESI+) m/z 442 (M+H)$^+$. Anal. found for C$_{23}$H$_{24}$ClN$_3$O$_2$S: C, 62.18; H, 5.46; N, 9.47; Cl, 8.40; S, 7.02.

EXAMPLES 8–9

N-(4-Chlorobenzyl)-1-methyl-4-oxo-6-(4-thiomorpholinyl-methyl)-1,4-dihydro-3-quinolinecarboxamide (221 mg) from Example No. 7 is dissolved in dry CH$_2$Cl$_2$ (15 mL) and the solution is cooled to 0° C. A solution of mCPBA (258 mg) in dry CH$_2$Cl$_2$ (5 mL) is added dropwise, maintaining the temperature of the solution between 0–2° C. The reaction is stirred at 0° C. for 2 h and then is allowed to warm to room temperature. The reaction is quenched with saturated NaHSO$_3$ (2 mL) and stirred to for another hour. Dilution with water (10 mL) forms a white precipitate which is filtered. The crude solid is a mixture of the two products which are purified by column chromatography (MeOH/CH$_2$Cl$_2$, 1/49 to 3/97) to afford 37 mg (16%) of Example No. 8 and 54 mg (24%) of Example No. 9 as white solids.

EXAMPLE 8

N-(4-chlorobenzyl)-6-[(1,1-dioxo-1',4-thiazinan-4-yl)methyl]-1-methyl-4-oxo-1,4-dihydro-3-quinolinecarboxamide.

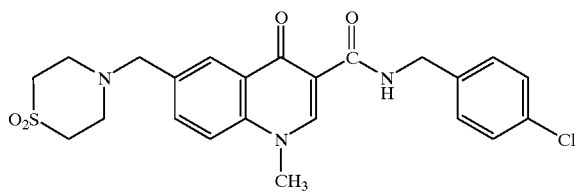

Physical characteristics are as follows:
Mp 245–247° C.; $^1$H NMR (DMSO-d$_6$) δ 10.42, 8.88, 8.26, 7.83, 7.42–7.34, 4.56, 4.03, 3.85, 3.11, 2.90; IR (drift) 1916, 1662, 1610, 1569, 1539, 1498, 1326, 1317, 1289, 1268, 1123, 1107, 805, 796, 661 cm$^{-1}$. Anal. Found for C$_{23}$H$_{24}$ClN$_3$O$_4$S: C, 58.05; H, 5.06; N, 8.78; Cl, 7.55.

EXAMPLE 9

N-(4-chlorobenzyl)-1-methyl-4-oxo-6-[( 1-oxo-1',4-thiazinan-4-yl)methyl]-1,4-dihydro-3-quinolinecarboxamide.

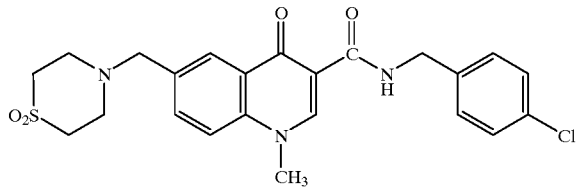

Physical characteristics are as follows:
Mp 249–251° C.; $^1$H NMR (DMSO-d$_6$) δ 10.42, 8.87, 8.26, 7.82, 7.42–7.34, 4.56, 4.02, 3.74, 2.91–2.83, 2.74–2.62; IR (drift) 2818, 2351, 1974, 1932, 1656, 1604, 1574, 1551, 1500, 1363, 1336, 1054, 1027, 838, 809 cm$^{-1}$. Anal. Found for C$_{23}$H$_{24}$ClN$_3$O$_3$S: C, 60.09; H, 5.30; N, 9.03; Cl, 7.90.

EXAMPLE 10

N-(4-chlorobenzyl)-8-fluoro-1-methyl-6-(4-morpholinylmethyl)-4-oxo-1,4-dihydro-3-quinolinecarboxamide

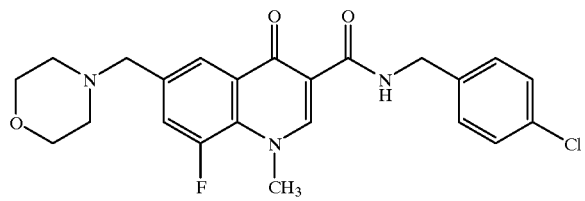

To a solution of N-(4-chlorobenzyl)-8-fluoro-4-hydroxy-6-(4-morpholinylmethyl)-3-quinolinecarboxamide, (can be prepared according to the procedure described in PCT patent application, WO99/32450) (147 mg) in anhydrous DMF (3 mL) is added K$_2$CO$_3$ (71.2 mg) followed by CH$_3$I (0.026 mL). The reaction mixture is stirred at room temperature for 30 min, then poured into H$_2$O (40 mL) to precipitate the product. The solid is collected, adsorbed onto silica, and chromatographed (1% MeOH in CH$_2$Cl$_2$ (2L)). Fractions homogenous by TLC are combined and concentrated to afford 55.3 mg of the title compound as a white solid.

Physical characteristics are as follows:
Mp 187–189° C.; $^1$H NMR (300 MHz, DMSO-d$_6$) δ 10.28, 8.77, 8.09, 7.65, 7.38, 4.56, 4.17, 3.58, 2.38; IR (drift) 1659, 1603, 1578, 1556, 1550, 1543, 1499, 1366, 1348, 1278, 1134, 1117, 865, 809, 797 cm$^{-1}$; HRMS (FAB) calcd for C$_{23}$H$_{23}$ClFN$_3$O$_3$+H$_1$ 444.1490, found 444.1484.

What is claimed is:

1. A compound of formula I

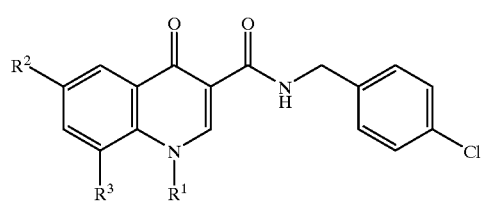

Wherein
R$^1$ is C$_{1-7}$ alkyl, optionally substituted by hydroxy or NR$^4$R$^5$;
R$^2$ is C$_{1-7}$ alkyl substituted by hydroxy or NR$^4$R$^5$;
R$^3$ is H, F or C$_{1-7}$ alkoxy;
R$^4$ and R$^5$ together with N are a 5- or 6-membered heterocyclic moiety having 1–3 heteroatoms selected from the group consisting of nitrogen, oxygen and sulfur in which sulfur may be substituted by one (1) or two (2) oxygen atoms; and a pharmaceutically acceptable salt thereof.

2. A compound of claim 1 wherein R$^1$ is C$_{1-4}$ alkyl, optionally substituted by hydroxy; R$^2$ is C$_{1-5}$ alkyl substituted by hydroxy or morpholine; and R$^3$ is H or F.

3. A compound of claim 1 which is
(a) N-(4-chlorobenzyl)-6-(3-hydroxy-1,1-dimethylpropyl)-1-methyl-4-oxo-1,4-dihydro-3-quinolinecarboxamide;

(b) N-(4-chlorobenzyl)-1-methyl-6-(4-morpholinylmethyl)-4-oxo-1,4-dihydro-3-quinolinecarboxamide;

(c) N-(4-chlorobenzyl)-1-(2-hydroxyethyl)-6-(3-hydroxypropyl)-4-oxo-1,4-dihydro-3-quinolinecarboxamide;

(d) N-(4-chlorobenzyl)-6-(3-hydroxypropyl)-1-methyl-4-oxo-1,4-dihydro-3-quinolinecarboxamide;

(e) 1-(tert-butyl)-N-(4-chlorobenzyl)-6-(3-hydroxypropyl)-4-oxo-1,4-dihydro-3-quinolinecarboxamide;

(f) N-(4-chlorobenzyl)-6-[(1,1-dioxo-1',4-thiazinan-4-yl)methyl]-1-methyl-4-oxo-1,4-dihydro-3-quinolinecarboxamide;

(g) N-(4-chlorobenzyl)-1-methyl-4-oxo-6-[( 1-oxo-1',4-thiazinan-4-yl)methyl]-1,4-dihydro-3-quinolinecarboxamide;

(h) N-(4-chlorobenzyl)-8-fluoro-1-methyl-6-(4-morpholinylmethyl)-4-oxo-1,4-dihydro-3-quinolinecarboxamide; or a pharmaceutically acceptable salt thereof.

4. A compound of claim 1 which is (a) N-(4-chlorobenzyl)-6-(3-hydroxy-1,1-dimethylpropyl)-1-methyl-4-oxo-1,4-dihydro-3-quinolinecarboxamide;

(b) N-(4-chlorobenzyl)-1-methyl-6-(4-morpholinylmethyl)-4-oxo-1,4-dihydro-3-quinolinecarboxamide;

(c) N-(4-chlorobenzyl)-1-(2-hydroxyethyl)-6-(3-hydroxypropyl)-4-oxo-1,4-dihydro-3-quinolinecarboxamide;

(d) N-(4-chlorobenzyl)-6-(3-hydroxypropyl)-1-methyl-4-oxo-1,4-dihydro-3-quinolinecarboxamide;

(e) N-(4-chlorobenzyl)-6-[(1,1-dioxo-1',4-thiazinan-4-yl)methyl]-1-methyl-4-oxo-1,4-dihydro-3-quinolinecarboxamide;

(f) N-(4-chlorobenzyl)-1-methyl-4-oxo-6-[(1-oxo-1',4-thiazinan-4-yl)methyl]-1,4-dihydro-3-quinolinecarboxamide;

(g) N-(4-chlorobenzyl)-8-fluoro-1-methyl-6-(4-morpholinylmethyl)-4-oxo-1,4-dihydro-3-quinolinecarboxamide; or a pharmaceutically acceptable salt thereof.

5. A compound of claim 1 which is (a) N-(4-chlorobenzyl)-1-methyl-6-(4-morpholinylmethyl)-4-oxo-1,4-dihydro-3-quinolinecarboxamide;

(b) N-(4-chlorobenzyl)-6-(3-hydroxypropyl)-1-methyl-4-oxo-1,4-dihydro-3-quinolinecarboxamide;

(c) N-(4-chlorobenzyl)-6-[(1,1-dioxo-1',4-thiazinan-4-yl)methyl]-1-methyl-4-oxo-1,4-dihydro-3-quinolinecarboxamide;

(d) N-(4-chlorobenzyl)-1-methyl-4-oxo-6-[(1-oxo-1',4-thiazinan-4-yl)methyl]-1,4-dihydro-3-quinolinecarboxamide;

(e) N-(4-chlorobenzyl)-8-fluoro-1-methyl-6-(4-morpholinylmethyl)-4-oxo-1,4-dihydro-3-quinolinecarboxamide; or a pharmaceutically acceptable salt thereof.

6. A compound of claim 1 which is N-(4-chlorobenzyl)-1-methyl-6-(4-morpholinylmethyl)-4-oxo-1,4-dihydro-3-quinolinecarboxamide, or a pharmaceutically acceptable salt thereof.

7. A method of treating infections from herpesviruses which comprises administering to a patient in need thereof an effective amount of a compound of formula I as shown in claim 1.

8. The method of claim 7 wherein said herpesviruses is herpes simplex virus types 1, herpes simplex virus types 2, varicella zoster virus, cytomegalovirus, Epstein-Barr virus, human herpes viruses 6, human herpes viruses 7 or human herpes viruses 8.

9. The method of claim 7 wherein said herpesviruses is herpes simplex virus types 1, herpes simplex virus types 2, varicella zoster virus, cytomegalovirus, Epstein-Barr virus, human herpes viruses 7 or human herpes viruses 8.

10. The method of claim 7 wherein said herpesviruses is human cytomegalovirus.

11. The method of claim 7 wherein the effective amount of a compound of claim 1 is administered orally, parenterally or topically.

12. The method of claim 7 wherein the effective amount of a compound of claim 1 is in an amount of from about 0.1 to about 300 mg/kg of body weight.

13. The method of claim 7 wherein the effective amount of a compound of claim 1 is in an amount of from about 1 to about 30 mg/kg of body weight.

14. A pharmaceutical composition which comprises an effective amount of a compound of claim 1 and a pharmaceutically acceptable carrier.

15. A method for inhibiting a viral DNA polymerase comprising contacting the polymerase with an effective inhibitory amount of a compound of formula I as shown in claim 1.

16. A process for the preparation of the compound of claim 6 comprising the steps of a. heating a mixture of diethyl ethoxymethylenemalonate and N-(4-methyl-aminobenzyl)morpholine to provide diethyl 2-{[methyl-4-(4-morpholinylmethyl)anilino]methylene}malonate, b. adding a solution of diethyl 2-{[methyl-4-(4-morpholinylmethyl)anilino]methylene }malonate in toluene to a mixture of phosphorus pentoxide and methanesulfonic acid to provide ethyl 1-methyl-6-(4-morpholinylmethyl)-4-oxo-1,4-dihydro-3-quinolinecarboxylate, c. converting ethyl 1-methyl-6-(4-morpholinylmethyl)-4-oxo-1,4-dihydro-3-quinolinecarboxylate to 1-methyl-6-(4-morpholinylmethyl)-4-oxo-1,4-dihydro-3-quinolinecarboxylic acid, d. stirring 1-methyl-6-(4-morpholinylmethyl)-4-oxo-1,4-dihydro-3-quinolinecarboxylic acid with carbonyldiimidazole and dimethyl formamide, and e. reacting 4-chlorobenzylamine with the mixture of step d.

17. A compound useful as synthetic intermediates in the preparation of the compound of claim 6 which is (a) diethyl 2-{[methyl-4-(4-morpholinylmethyl)anilino]methylene }malonate.

* * * * *